United States Patent [19]
Roffe et al.

[11] Patent Number: 6,106,283
[45] Date of Patent: Aug. 22, 2000

[54] ROOT CANAL OBTURATION INSTRUMENT

[76] Inventors: Tara Roffe; Brian Roffe, both of 376 Yale Ave., Woodmere, N.Y. 11598-2051

[21] Appl. No.: 09/359,252

[22] Filed: Jul. 22, 1999

[51] Int. Cl.⁷ ...................................................... A61C 3/00
[52] U.S. Cl. ............................................. 433/32; 219/223
[58] Field of Search ................................ 433/32, 81, 102; 219/223, 226, 229, 231, 481

[56] References Cited

U.S. PATENT DOCUMENTS

| | | | |
|---|---|---|---|
| 1,370,524 | 3/1921 | Dumaine | 219/223 |
| 3,899,830 | 8/1975 | Malmin | 32/15 |
| 4,392,827 | 7/1983 | Martin | 433/32 |
| 4,480,996 | 11/1984 | Crovatto | 433/164 |
| 4,525,147 | 6/1985 | Pitz et al. | 433/224 |
| 4,527,560 | 7/1985 | Masreliez | 433/32 |
| 4,681,545 | 7/1987 | Lapcevic | 433/224 |
| 4,894,011 | 1/1990 | Johnson | 433/81 |
| 4,992,045 | 2/1991 | Beisel | 433/32 |
| 5,043,560 | 8/1991 | Masreliez | 219/497 |
| 5,067,900 | 11/1991 | McSpadden | 433/81 |
| 5,215,461 | 6/1993 | Riazi | 433/224 |
| 5,605,460 | 2/1997 | Heath et al. | 433/224 |
| 5,752,825 | 5/1998 | Buchanan | 433/32 |
| 5,893,713 | 4/1999 | Garman et al. | 433/32 |

*Primary Examiner*—Todd E. Manahan
*Attorney, Agent, or Firm*—Brian Roffe

[57] ABSTRACT

An apparatus for obturating a root canal including a first member having a frame and a heatable probe mounted to the frame to project outward from the frame and adapted for insertion into proximity of the root canal, and a second member for covering the heating probe. The second member is attachable to the first member in a position in which the second member covers the heating probe and is also movable from the position to expose the heating probe. A heating element may be arranged in connection with the frame for heating the heating probe and also, a battery may be arranged in the first member for providing power to the heating element. Preferably, a manual switch is provided to control the heating element and enable regulation of the temperature of the heating probe.

29 Claims, 5 Drawing Sheets

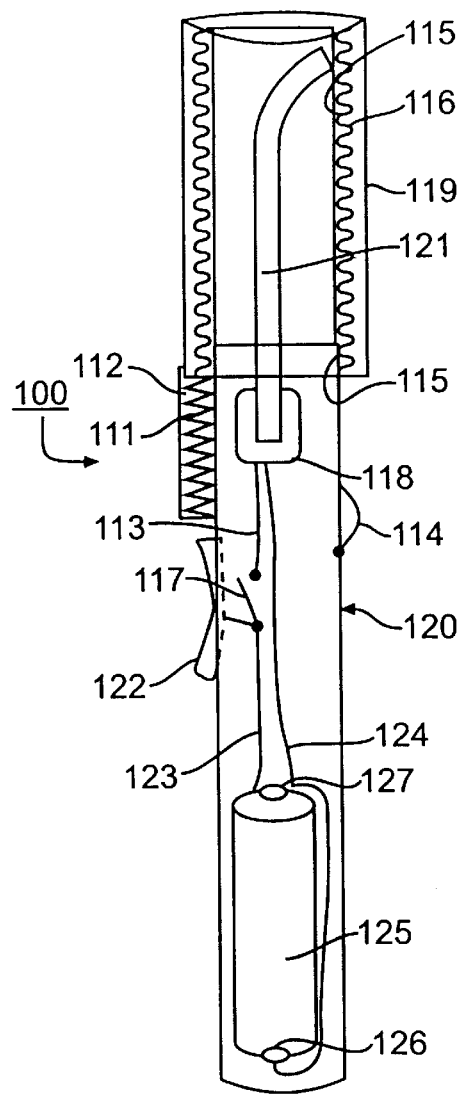
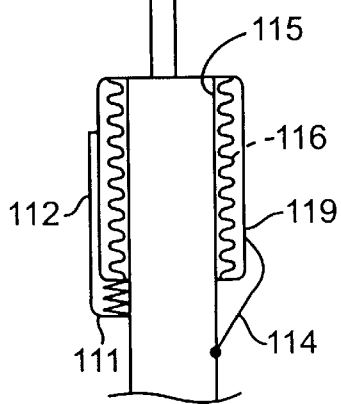
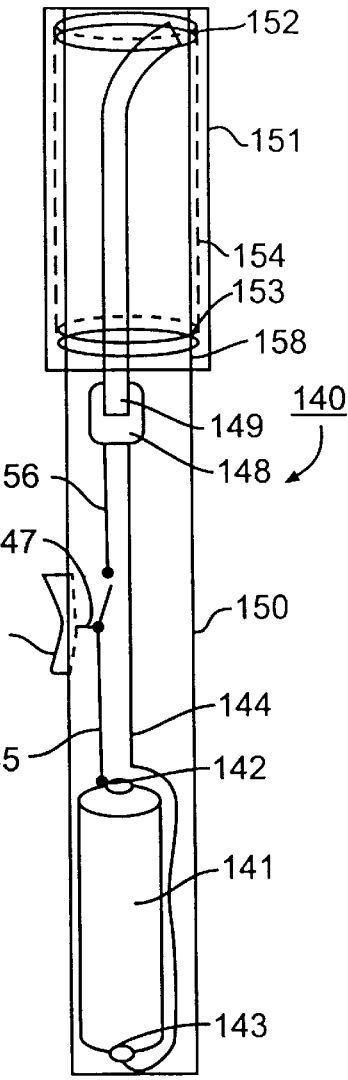
FIG. 3A
FIG. 3B
FIG. 4

ROOT CANAL OBTURATION INSTRUMENT

FIELD OF THE INVENTION

The present invention relates to an instrument for use in the final stage of root canal therapy and more particularly in the obturation of the root canal systems. The instrument sears off gutta percha in the root canal utilizing a controlled application of heat.

BACKGROUND OF THE INVENTION

At the present time, in the obturation of root canal systems during root canal therapy, it is usually necessary to sear off gutta percha, i.e., to apply heat to burn off unwanted filling material (excess gutta percha). This is usually accomplished by introducing a dental instrument, such as a so-called plastic instrument, into an existing flame, such as that provided by a Bunsen burner, to heat the same and then applying the heated plastic instrument to the pulp chamber of the tooth having excess gutta percha. In this manner, excessive gutta percha is burned off so that only an amount of gutta percha necessary in the root canal is present. It should be recognized that although gutta percha is a commonly used substance to fill root canals, other deformable or beat moldable material are occasionally used to fill the root canals, but gutta percha will be used hereinafter as synonymous with a filling material for the purposes of this application.

There are several problems with this conventional method. First, the burning flame of the Bunsen burner is a hazard that may ignite other flammable material. Second, the flame must be kept constantly burning during the obturation of the root canal in view of the fact that it is used intermittently during the obturation procedure and it is not cost effective to continually extnguish and relight the flame. Third, the flame is often of such magnitude that it frightens patients (who may not be used to undergoing a dental procedure in the vicinity of a burning flame). Fourth, this obturation method requires frequent transfer of the heated dental instrument between the flame and the patient's mouth. During such transfer(s), it is a continuous hazard that the instrument may inadvertently fall, burning something, more significantly and harmfully burning the mouth of the patient. Further, in view of the necessity of such transfer(s) between the flame and the patient's mouth, there is an obvious loss of heat, i.e., the instrument cools somewhat after it is removed from the flame and before it is used operatively in the patient's mouth. This loss of heat may be significant in view of the fact that the filling material, i.e., the gutta percha, will not melt if the instrument has cooled to a temperature below the melting temperature of the gutta percha In the prior art, the general endodontic process for filling a root canal in a tooth with gutta percha is described in U.S. Pat. Nos. 4,480,996 (Crovatto), 4,525,147 (Pitz et al.), 4,681,545 (Lapcevic), 4,894,011 (Johnson) and 5,067,900 (McSpadden).

OBJECTS AND SUMMARY OF THE INVENTION

Accordingly, it is an object of the present invention to provide a new and improved method and apparatus for searing off gutta percha during the obturation phase of root canal therapy.

It is another object of the present invention to provide a new and improved method and apparatus for searing off gutta percha during the obturation phase of root canal therapy that is safe and effective.

It is yet another object of the present invention to provide a new and improved method and apparatus for searing off gutta percha during the obturation phase of root canal therapy which substantially avoids the problems with the conventional method and apparatus mentioned above.

It is still another object of the invention to provide a new and improved dental instrument that includes a metal component that is heatable in a safe manner and can be applied in a safe manner to conduct dental treatment in a patient's mouth which requires the application of heat.

It is still another object of the present invention to provide a new and improved dental instrument that avoids the potentially obtrusive presence of a continually burning flame in proximity to the dental patient during dental procedures.

Accordingly, the instrument in accordance with the invention comprises an elongate tube including electrically-powered heating means and a curved heating probe coupled to the heating means, and a detachable cover for covering the heating probe of the tube when the heating probe is not in use. The heating means may be either a battery or other electricity storage module housed within the tube or an electric unit having a cord for connection to an external power source. When activated, the heating means function to heat the heating probe that extends at one end of the tube and curves slightly beyond that end of the tube. The cover releasably engages with one end of the tube and is designed to fit over the heating probe but not in contact therewith so that it is possible to heat the heating probe while it is still housed within the cover. The cover defines a space in an interior thereof in which the heating probe is situated and heated by the heating means upon energization thereof. Thus, upon detaching of the cover from its engagement with the tube, the probe has already been heated and is ready for use. On the other hand, after use of the heating probe, it is only necessary to place the cover into engagement with the end of the tube, at which time, the heating means can be turned off if desired. Alternatively, if the heating probe is to be re-used during the course of the dental treatment, the heating means can be maintained in an "on condition".

Thus, one basic embodiment of an apparatus for obturating a root canal comprises a first member comprising a frame, and a heatable probe mounted to the frame to project outward from the frame and adapted for insertion into proximity of the root canal, and a second member for covering the heating probe. The second member is attachable to the first member in a position in which the second member covers the heating probe, and thereby prevents injury resulting from the heated probe, and is also movable from the position to expose the heating probe and enable use thereof. The first member may be a cylindrical tube and the second member a cover adapted to fit over the upper end of the cylindrical tube. To maximize the use of the heating probe for accessing the root canal, the heating probe preferably has a first portion extending parallel to axis of the first member and a second portion adjacent the first portion extending at an angle to the first portion. The thickness of the second portion, including its end, is dimensioned to enable entry into the root canal (the range of sizes of which is known to those skilled in the art) and thus has a very small thickness.

To beat the heating probe, heating means may be arranged in connection with the frame and powered by appropriate power means, either internal such as a battery housed in the frame, or appropriate electrical components to enable connection to a power cord connecting to an outlet. To maintain the temperature of the heating probe at a desired temperature, high enough to enable obturation, control means are provided for controlling the heating means, e.g., a switch electrically coupled to and interposed between the heating means and the power means.

In one embodiment, attachment means are provided for removably attaching the second member to the first member. The attachment means may comprise a first circumferentially extending snap arranged on an exterior surface of the first member and a second cooperating circumferentially extending snap arranged on an interior surface of the second member. Further, the attachment means preferably comprise recesses formed in a lower region of the first snap and projections formed in a lower region of the second snap.

In an enhanced embodiment, securing means are provided for securing the second member to the first member to prevent inadvertent separation of the second member from the first member.

In another embodiment, the second member is a retractable cover connected to the first member and has a first position in which the cover covers the heating probe and a second retracted position in which the heating probe is exposed. Displacement means are provided for enabling the second member to move between the first position and the second position. The displacement means may comprise cooperating threads arranged on an outer periphery of the first member and on an inner surface of the cover. Locking means may also be provided for locking the cover in the second position, e.g., a flexible, metal bracket arranged on an outer peripheral surface of the first member whereby one end of the bracket is attached to the outer surface of the first member and an opposite end of the bracket is free and displaceable by flexure toward and away from the outer surface such that at least a portion of the cover is insertable between the free end of the bracket and the outer surface of the first member. Biasing means such as a spring may also be provided for maintaining the cover in the first position.

In yet another embodiment, the second member is a cover slidably connected to the first member. The cover comprises axially extending channels and a respective slot at each end of each channel. The slots extend circumferentially around at least a portion of an inner surface of the cover. The first member includes projections at an upper end, each projection being sidable within a respective channel and slots associated therewith.

Another embodiment of the apparatus for obturating a root canal, comprises housing means defining an interior compartment, e.g., a tubular structure, a displaceable unit comprising a heatable probe adapted for insertion into proximity of the root canal, and heating means for heating the probe, and displacement means for moving the unit from a first position in which the probe is in the compartment to a second position in which the probe is outside of the compartment. The unit can include a frame on which the heating means and the probe are mounted and a battery coupled to the heating means for supplying power to the heating means. The displacement means may comprise an appendage attached to the unit and extending outside of the compartment, e.g., a circular disc and a shaft extending from the disc to the unit. Cooperating securing means are preferably arranged on the housing means and the unit for securing the unit in the first position in which the probe is exterior of the compartment and the second position in which the probe is inside the compartment.

Another similar embodiment of the instrument includes a pushbutton connected to the unit while the housing means including a slot having a pair of circular regions adapted to receive a spherical part of the pushbutton. The pushbutton further includes a rigid component connected to the unit and a spring interposed between the rigid component and the pushbutton.

BRIEF DESCRIPTION OF THE DRAWINGS

The invention will be described with reference to the accompanying non-limiting drawings wherein:

FIG. 3A is a cross-sectional view of another embodiment of the instrument in accordance with the invention;

FIG. 3B is a view of the embodiment of the instrument in accordance with the invention shown in FIG. 3 with the cover in its retracted position;

FIG. 4 is a cross-sectional view of yet another embodiment of the instrument in accordance with the invention;

DETAILED DESCRIPTION OF THE PREFERRED EMBODIMENTS

Figure 1:
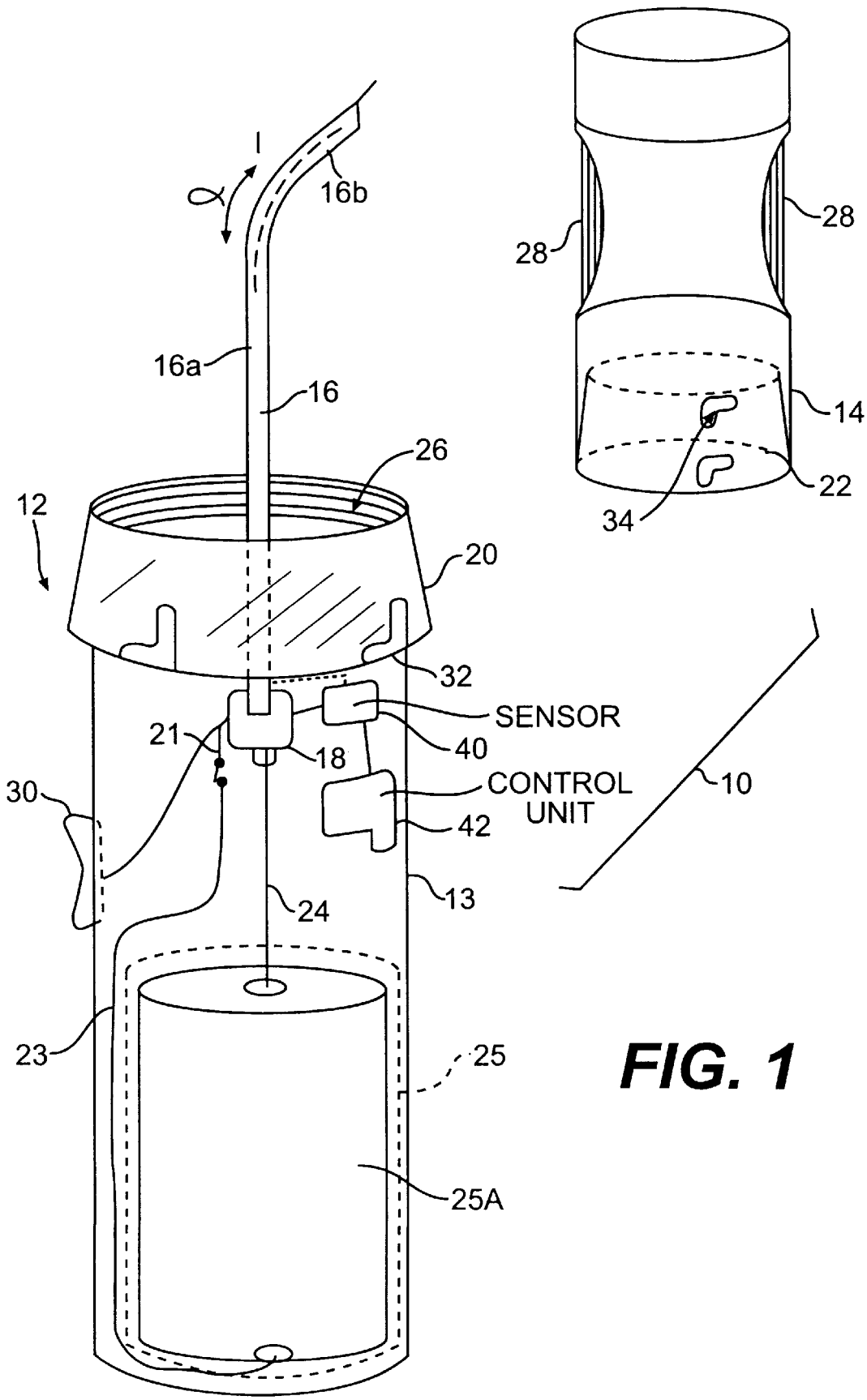
FIG. 1 is a perspective view of the apparatus in accordance with the invention in which the cover member is separate from the base member.

Referring to the accompanying drawings wherein like reference numerals refer to the same or similar elements, the apparatus in accordance with the invention is denoted generally at 10 and comprises two members, an elongate substantially cylindrical member 12 and a cover member 14 adapted to mate with the cylindrical member or tube 12. Generally, the cylindrical member 12 includes a frame 13, a heatable probe 16 mounted on the frame 13 in an outwardly extending position from one end 26 of the frame 13 and heating means 18 for heating the probe 16. The probe 16 is made of any suitable heatable material such as a metal, and is ideally provided with a curvature at an end distal from the frame 13 as shown in FIG. 1. The heating means 18 may comprise a conventional heating unit that may be thermally coupled to the heating probe 16 so that heat generated by the heating unit is transferred to the heating probe 16. In the alternative, the heating means 18 may be a simple seat made of an electrically conductive material or any other appropriate means for heating the probe 16 upon completion of an electrical circuit therewith.

The frame 13 houses power means for providing power to the heating means 18, such as a battery 25A received in a battery compartment 25 defined in frame 13. When activated to supply power to the heating unit 18, battery 25A provides electrical power through electrical coupling means such as wires 23,24 extending between the terminals of the battery 25A and the heating means 18. The frame 13 may also comprise appropriate thermal insulation to prevent the outer surfaces of the cylindrical member 12 from becoming hot. The connections of the wires 23,24 to the terminals of the battery 25A are common knowledge and within the skill of one versed in the art.

To provide for selective heating of the probe 16 by the heating means 18, i.e., heating of the probe 16 when desired, an electrical switch 21 is situated in connection with the wire from one of the terminals of the battery 25A to the heating means 18. When the switch 21 is closed, an electrical circuit is completed between the terminals of the battery 25A and the heating means 18 through wires 23,24 so that the heating means 18 are enabled to heat the probe 16. However, when the switch 21 is open, the electrical circuit is not completed and the heating means 18 are not operable to heat the probe 16. The activation of the switch 21 is caused by the placement of a switch 30 on an outer wall of the frame 13 whereby the switch 30 is positionable in at least two different positions, one in which switch 21 is closed and the other in which switch 21 is open. Depressing switch 30 will therefore enable heating of probe 16 while release of the switch 30 will cease heating of the probe 16.

The construction of switches 21,30 may be any conventional manually activated electrical switches designed to enable manual control of the heating means 18. For example, the control means of the heating means 18 may be constituted by a control on the battery 25A which toggles the power output of the battery 25A so that when the battery 25A supplies power, the heating means 18 are operable and when the power is toggled, power is not supplied to the heating means 18.

In the alternative, as shown in FIG. 1, a temperature sensor 40 is placed in conjunction with the heating means 18 (or probe 16 shown in dotted lines) in order to measure the temperature of the probe 16. As such, a control unit 42 is arranged in association with frame 13, and coupled to temperature sensor 40, in order to receive the measured temperature of the probe 16 from the temperature sensor 40 and activate the heating means 18 in order to provide for a desired temperature of the probe 16. The temperature of the probe 16 may thus be maintained in a defined range of temperature whereby if the temperature of the probe 16 falls outside of the range, the control unit 42 functions to cause the heating means 18 to heat the probe 16 until the temperature of the probe 16 is either within the range or just beyond the range. At this point, the control unit 42 would direct the heating means 18 to cease operation. The exact temperature to which the probe 16 is heated would depend on several factors, bearing in mind that the tip of the heating probe should preferably be red hot. Thus, the factors include the material of the probe 16, or at least the material of the tip of the probe 16 if the probe is made of different materials. In this regard, the probe can be made of different materials, the arrangement of which is designed to maximize the heat transmission to the tip. Other control schemes could also be employed by the control unit 42, e.g., a timed operation whereby the control unit activates the heating means 18 for a set period of time at periodic intervals.

To restrict the exposure of the heating probe 16 only to the times when it is required for the root canal treatment, attachment means are provided for detachably/releasably coupling the cover 14 to the end 26 of the member 12 from which the heating probe 16 projects. Specifically, a cooperating snap 20 is arranged on an exterior surface of the member 12 proximate the end 26 of the member 12 and a cooperating snap 22 is arranged on an interior surface of the cover 14. The snaps 20,22 extending circumferentially around the corresponding surface. To provide a secure attachment, L-shaped recesses 32 are formed in a lower region of the snap 20 and projections 34 are formed in the lower region of the snap 22. For attachment, the projections 34 are received in a respective one of the recesses 32 and the cover 14 is turned such that the projections 34 are grasped by edges of the recesses 32 and retained therein. Other appropriate attachment means and securing means are of course possible to use in the invention without deviating from the scope of the invention. The cover 14 enables the heating probe 16 to be heated while it is still housed within the cover 14 thereby avoiding several problems endemic in the prior art root canal treatment, viz., having an exposed flame which may frighten patients and the necessity to transfer an instrument from a heating source a relatively long distance into the patient's mouth.

Figure 2:
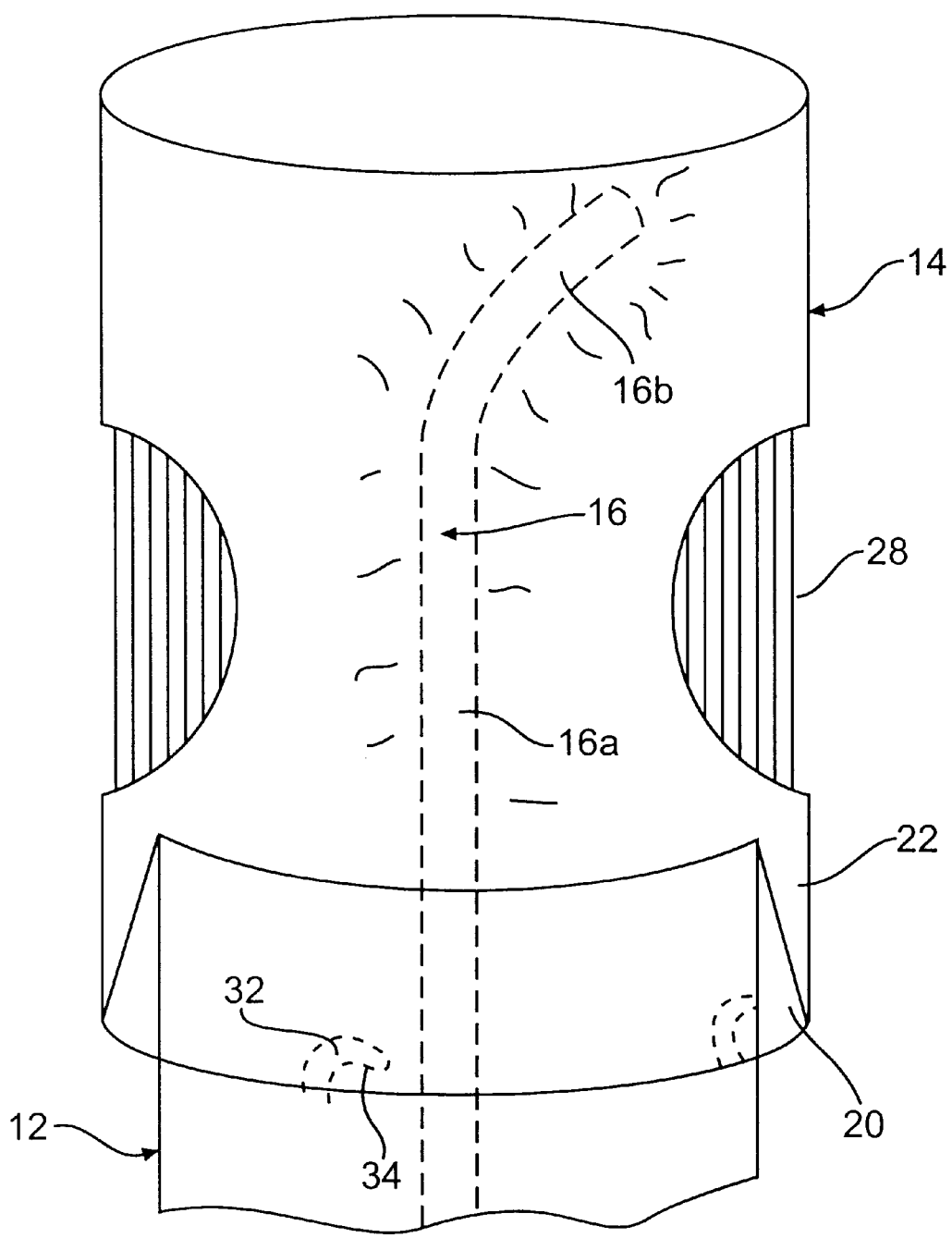
FIG. 2 is a partial view of the apparatus in accordance with the invention in which the cover member is in engagement with the base member and the heating probe is being heated.

The cover 14 is "over-sized", i.e., has a size so that it fits over the heating probe 16 without contacting the same (se FIG. 2). Further, cover 14 includes thumb grips 28, i.e., parallel ridges or indentations, to aid in removal of the cover 14 from its position in engagement with member 12. Alternative thumb grips such as roughenings may also be provided on the outer surface of the cover 14.

As noted above, switch 30 controls the opening and closing of the switch 21 thereby controlling the operation of the heating means 18 for activating the same to heat the heating probe 16, when desired. When not in use, the switch 30 is in its off position so that switch 21 is open and the heating probe 16 is not heated and may cool. The switch 30 may be provided with a locking mechanism (not shown) to lock the switch 30 in the on position and/or the off position. If the switch 30 is lockable in the off position, then it will be necessary to maintain pressure on the switch 30 during use of the heated probe 16. On the other hand, if the switch 30 is lockable in the on position, then it will be possible to use the heated probe 16 without concern as to continually applying pressure on the switch 30, which may be advantageous in certain situations, i.e., expected extended use.

Instead of the battery 25A, alternative electrical power means may be used. These may include an electrical unit housed within the member 12 and a cord for connecting the electrical unit to external electrical sources. In this instance, the size of the instrument can be made quite small in view of the absence of the battery and the continual miniaturization of electrical components.

In the illustrated embodiments, the heating probe 16 has a straight portion 16a adjacent to the end 26 of the member 12 and another straight portion 16b arranged at an angle a with respect to the portion 16a. By providing the heating probe 16 with such an angle, it is easier to access the gutta percha in the root canal which must be seared off at the end of the root canal treatment. Although such an angle is preferred, it is nevertheless possible to construct the heating probe 16 to be entirely straight and oriented either parallel or even coincident with the axis of the member 12 or at an angle to the axis of the member 12.

It should be understood by those skilled in the art that the manner in which the heating probe 16 is heated is not limited solely to the use of a battery 25A and an electrical heating means 18 electrically coupled thereto and both of which are housed within an interior of the member 12. Rather, it is within the scope of the invention that any conventional and/or suitable heating means, battery-powered or powered by an external electrical source or located entirely exterior of the tube, can be used to provide heat energy to the heating probe. Preferably, as noted above, the application of heat to the heating probe 16 will be controlled by appropriate heat regulation means to prevent the heating probe from being heated to an excessive temperature or to a temperature below the required temperature to melt or burn away the excessive gutta percha in the root canal being operated on in the patient's mouth.

In one possible embodiment, it is foreseen that the heating probe 16 can be heated by microwave radiation applied from a microwave source, the remaining portions of the apparatus being constructed to be microwave-durable to prevent damage from exposure in the microwave field and/or being shielded during irradiation of the apparatus. Of course, the heating probe 16 should be constructed from a material which will be heated during exposure to a microwave field, which type of material can be readily ascertained.

It is also recognized that although gutta percha is the most common material used to fill a root canal and upon which the instrument in accordance with the invention will be applicable, the invention is equally applicable on other root canal filling materials that are spread and condensed in the root canal and which require heat in order to eliminate excess material.

In the embodiment shown in FIGS. 3A and 3B, the instrument in accordance with the invention is designated generally as 100 and comprises a narrow cylindrical member tube 120 having a compartment for receiving and retaining a battery 125 such as an AA or AAA size having a positive terminal 127 and a negative terminal 126. A wire 124 is electrically coupled at one end to the negative terminal 126 of the battery 125 and electrically coupled at a second end to heating unit 118. A second wire 123 is electrically coupled at a first end to the positive terminal 127 of the battery 125 and connects to a switch 117. Switch 117 is controlled by an on-off knob or switch 122 such that when the knob 122 is in its on position, the switch 117 is closed and engages a third wire 113 electrically coupled to the heating unit 118. In this manner, a complete electrical circuit is formed including the heating unit 118 and the battery 125. A heating probe 121 is coupled to the heating unit 118 and is heated upon activation of the heating unit 118 by the battery 125.

In this embodiment, instead of the removable cover 14 as shown in FIGS. 1 and 2, a retractable cover 119 is coupled to the tube 120. This embodiment thus has the advantage that the cover is never completely separated from the tube 120 and cannot be lost or misplaced. Again, as in the embodiment of FIGS. 1 and 2, it is possible to heat the probe 16 while it is still housed within the cover 119. However, in this embodiment, instead of removing the cover to use the probe, it is simply possible to twist the cover 119 with respect to the tube 120 thereby causing the cover 119 to move downward along an outer periphery of the tube 120 toward the battery 125 (in the illustrated embodiment). The twisting of the cover 119 with respect to the tube 120 is facilitated by the presence of cooperating threads 115,116 on the inner surface of the cover 119 and an uppermost portion of the outer peripheral surface of the tube 120. For the sake of simplicity and easy access, it is preferable to provide only a minimum number of threads.

In this embodiment, it is necessary to ensure that the cover 119 remains in its position whether it be the probe-exposing position as shown in FIG. 3B or the probe-concealing position as shown in FIG. 3A. To this end, the instrument 100 includes locking means for locking the cover 119 in the probe-exposing position. These locking means comprise a flexible, metal bracket 114 arranged on an outer peripheral surface of the tube 120. One end of the bracket 114 is attached to the outer surface of the tube 120 and the other end of the bracket 114 is free and displaceable by flexure toward and away from the outer surface. In this manner, upon the descent of the cover 119, at least a portion of the cover 119 is insertable between the free end of the bracket 114 and is retained securely in the probe-exposing position thereby. Other locking means, such as a snap-fit connection, latch, belt, tongue and groove arrangement as well as any other releasable attachment means such as hook and loop fasteners (e.g., VELCRO™), may be used in the invention without deviating from the scope of the invention.

To maintain the cover 119 in its probe-concealing position as shown in FIG. 3A, the instrument 100 includes biasing means such as a spring 111 contained in a housing 112. One end of the spring 111 is exposed through an opening in the housing 112 and engages the lower surface of the cover 119.

In the embodiment shown in FIG. 4, the instrument in accordance with the invention is designated generally as 140 and comprises a narrow cylindrical member or tube 150 having a compartment for receiving and retaining a battery 141 such as an AA or AAA size having a positive terminal 142 and a negative terminal 143. A wire 144 is electrically coupled at one end to the negative terminal 143 of the battery 141 and electrically coupled at a second end to heating unit 148. A second wire 145 is electrically coupled at a first end to the positive terminal 142 of the battery 141 and connects to a switch 147. Switch 147 is controlled by an on-off knob or switch 146 such that when the knob 146 is in its on position, the switch 147 is closed and engages a third wire 156 electrically coupled to the heating unit 148. In this manner, a complete electrical circuit is formed including the heating unit 148 and the battery 141. A heating probe 149 is coupled to the heating unit 148 and is heated upon activation of the heating unit 148 by the battery 141.

In this embodiment, instead of the removable cover 14 as shown in FIGS. 1 and 2 and the a retractable cover 119 shown in FIGS. 3A and 3B, a sliding cover 151 is provided. Cover 151 includes a plurality of axially extending channels 154 formed in an inner circumferential surface and a respective slot 152,153 at the ends of each channel 154. Slots 152,153 extend circumferentially around at least a portion of the inner surface of the cover 151. The tube 150 includes projections 158 at an upper end, each slidable within a respective channel 154 and the associated slots 152,153. The number of projections 158 corresponds to the number of channels 154. This embodiment thus has the advantage that the cover 151 is never completely separated from the tube 150 and cannot be lost or misplaced. As in the embodiments described above, it is possible to heat the probe 149 while it is still housed within the cover 151.

In this embodiment, in a storage and optional heating state, each projection 158 is situated in a respective lower slot 153. To use the probe 149, the cover 151 is twisted with respect to the tube 150 thereby causing the projections 158 to slide within the slots 153 until they align with a respective channel 154. The cover 151 is drawn downward toward the tube 150 along an outer periphery of the tube 150 until the projections 158 align each with a respective upper slot 152. The cover 151 is then twisted to cause the projections 158 to enter into the slots 152 and thereby retain the cover 151 is a position in which the probe 149 is exposed and available for use.

In this embodiment, it would be desirable to ensure that the cover 151 remains in its position whether it is the probe-exposing position or the probe-concealing position. To this end, the cover 151 or the tube 150 could include locking means for locking the cover 151 in its position. For example, such locking means might be provided by spring-biasing the projections 158 and providing a deeper recess at an end of each slot 152,153. The spring would bias the projections outward into these slots and prevent inadvertent displacement of the cover 151 during operation.

Figures 5A, 5B:
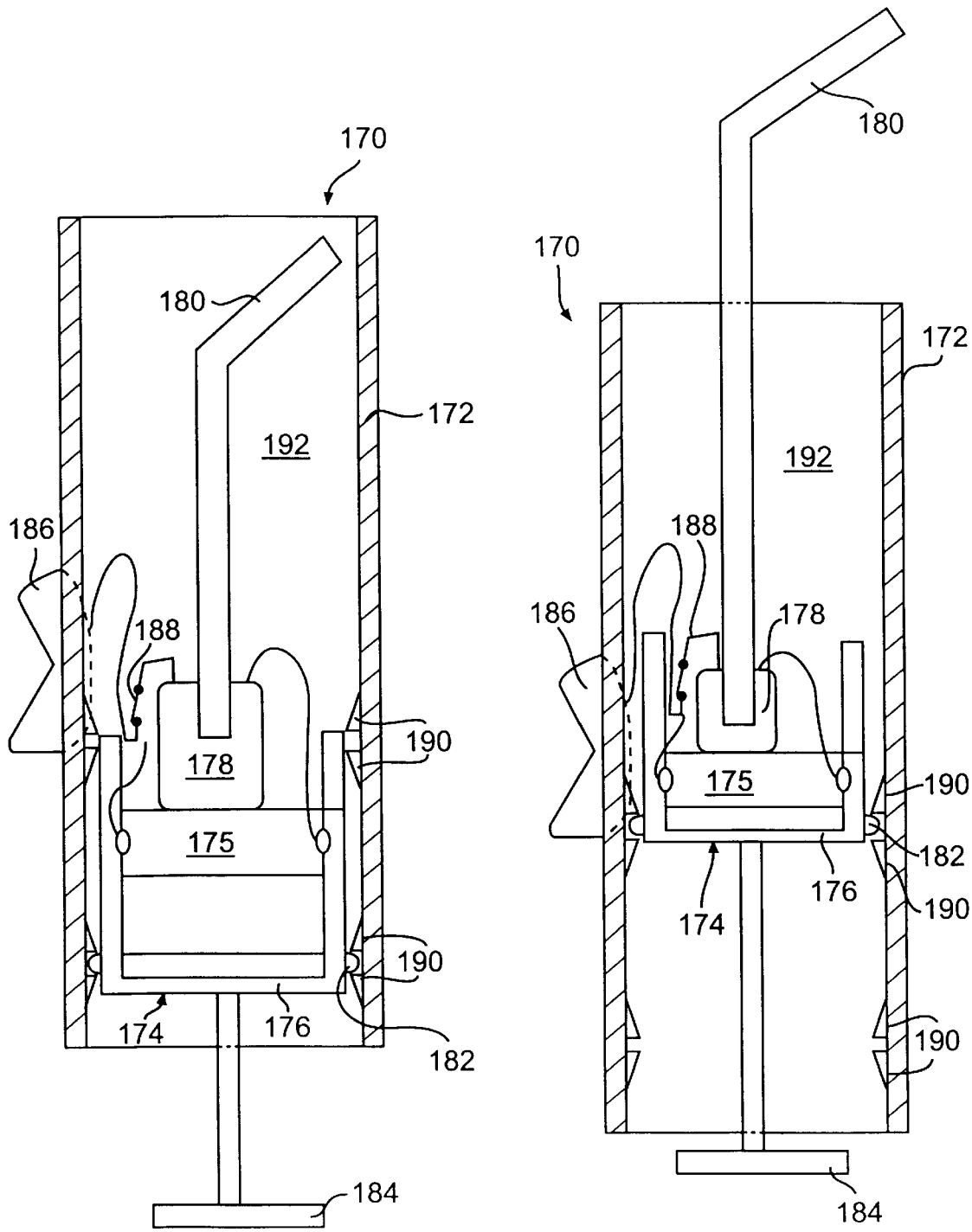
FIG. 5A is a cross-sectional view of another embodiment of the instrument in accordance with the invention in which the heating probe is housed in the instrument.
FIG. 5B is a cross-sectional view of the embodiment shown in FIG. 5A wherein the heating probe is exposed and available for use.

In the embodiment shown in FIGS. 5A and 5B, the instrument in accordance with the invention is designated generally as 170 and comprises a narrow cylindrical member or tube 172 having a displaceable unit or sled 174. Displacement unit 174 includes a frame 176 on which a battery 175 is mounted, heating means 178 and a probe 180 are stationarily arranged for movement with the frame 174. The frame 174 also includes protrusions 182 extending radially outward and a manually accessible appendage 184. Tube 172 includes a switch 186 on an exterior surface controlling an electrical switch 188 which when closed provides electrical current from the battery 175 to the heating means 178 (see FIG. 5B). Tube 172 also includes projections 190 on an interior surface for cooperating with the protrusions 182 on the frame 176.

In its storage position shown in FIG. 5A, the probe 180 is situated in the interior chamber 192 defined in the tube 172. Upon depressing switch 186, the electrical switch 188 is closed thereby energizing the heating means 178 and causing the probe 180 to heat up. (Heating of the probe 180 may occur while the probe is in the compartment 192 and/or when the probe 180 is outside of the compartment 192 as shown in FIG. 5B.) When the probe is needed for the root canal procedure, the dentist depresses appendage 184 causing release of the protrusions 182 from between the lower set of projections 190 and allowing the unit 174 to slide (upward) within the tube 172 until the protrusions 182 are secured between the upper set of projections 190. To this end, the projections 190 and protrusions 182 may be appropriately constructed in several known ways to allow for release of the unit 174 from a fixed position relative to the tube 172 only upon manual activation of the appendage 184. This will prevent inadvertent and unwanted movement of the unit 174, and thus the probe 180. Once the protrusions 182 are secured between the upper set of projections 190, the probe 180 is exterior of the tube 172 and ready for use. When the procedure is finished, the dentist pulls the appendage to release the protrusions 182 from the upper set of projections 190 and continues pulling until the protrusions 182 are situated between the lower set of projections 190.

It is also possible to construct the protrusions 182 and projections 190 to require twisting (rotation) of the appendage 184 to enable release of the protrusions 182 from the projections 190. Also, guide means for guiding the sliding movement of the unit 174 in the tube 172 should be provided.

Figure 6:
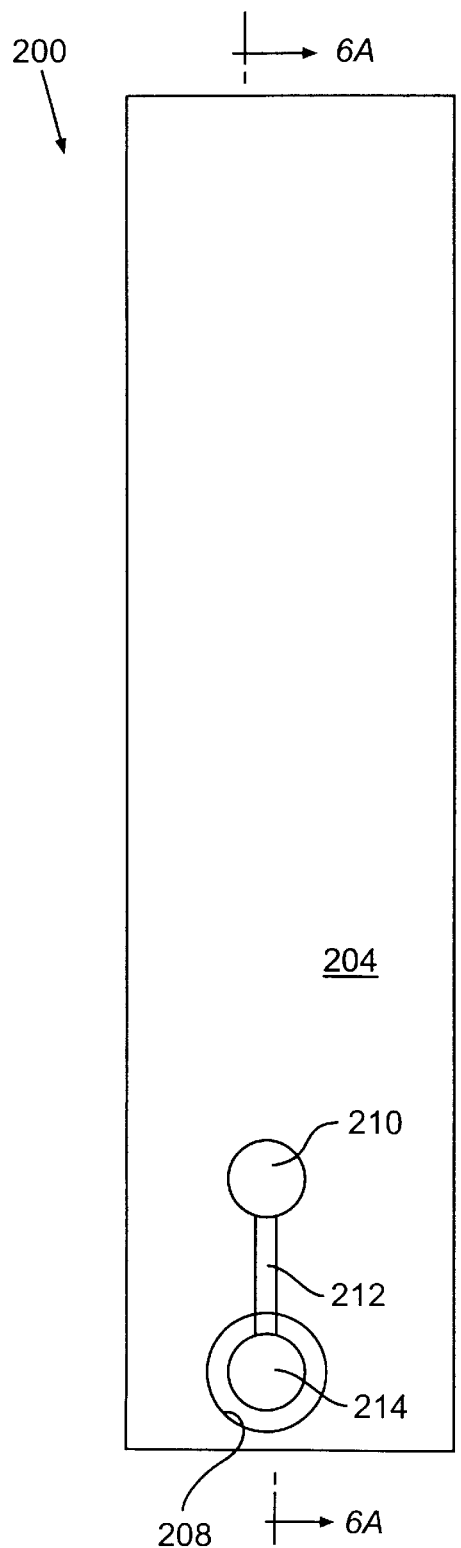
FIG. 6 is a front view of another embodiment of the instrument in accordance with the invention.
Figure 6A:
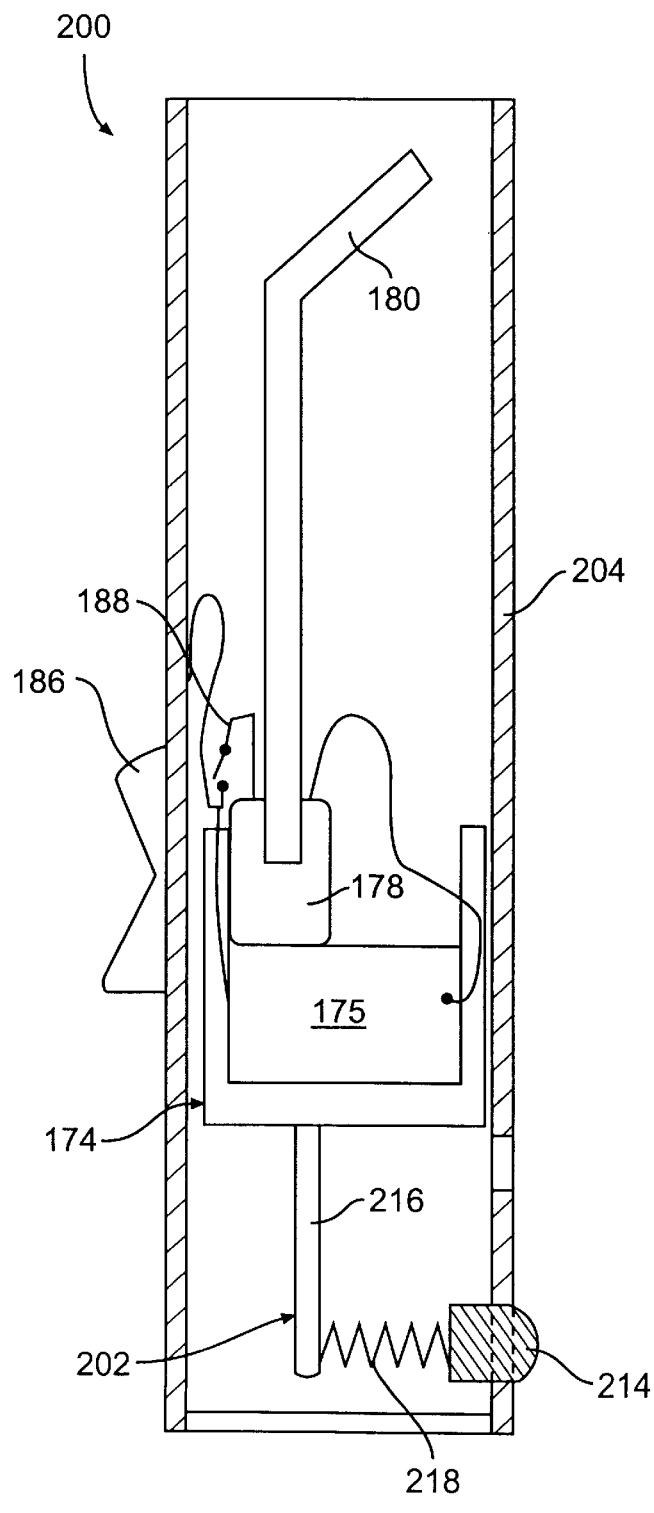
FIG. 6A is a cross-sectional view of the instrument shown in FIG. 6 taken along the line 6A—6A of FIG. 6

In another embodiment shown in FIGS. 6 and 6A, which is similar in most respects to the embodiment shown in FIGS. 5A and 5B and thus the same reference numerals are used to designate the same elements, instead of appendage 184, the instrument (designated 200) includes a pushbutton 202 and the tube 204 includes an elongate slot 206 having circular regions 208,210 and a straight portion 212 therebetween. The pushbutton 202 includes a spherical part 214 adapted to pass at least partially through the circular regions 208,210 a rigid component 216 connected to the unit 174 and a spring 218 coupling the spherical part 214 to the component 216.

In its storage position shown in FIG. 6A, the spherical part 214 of the pushbutton 202 is in the lower circular region 208. Upon depressing switch 186, the electrical switch 188 is closed thereby energizing the heating means 178 and causing the probe 180 to heat up although heating of the probe 180 may occur while the probe is in the compartment 192 and/or when the probe 180 is outside of the compartment 192. The dentist then presses spherical part 214 inward against the bias of spring 218 and then upward so that the spherical part 214 slides in the straight portion 212 into the upper circular region 210. The dentist releases the inward pressure on spherical part 214 so tat the spherical part 214 is urged outward upon expansion of spring 218 into the circular region 210. Movement of the pushbutton translates into movement of the unit 174 and thus inward and outward movement of the probe 180.

In the embodiments of FIGS. 5–6A, instead of providing unit 174 on which the battery 175, heating means 178 and probe 180 are mounted, it is possible to mount the battery 175 in a fixed position in the tube 172 such that only the heating means 178 and probe 180 are movable. The wires connecting the battery 175 to the heating means would be dimensioned to allow for movement of the heating means 178 relative to the battery 175. Also, as noted above, the battery could be replaced by appropriate electrical components to allow for an external power source, i.e., connections for a plug.

It will be understood that numerous modifications and substitution can be made to the above-described embodiments without deviating from the scope and spirit of the invention. Accordingly, the above-described embodiments are intended for the purpose of illustration and not as limitation.

We claim:

1. An apparatus for use in obturating a root canal, comprising
   a first member comprising
      a frame, and
      a heatable probe mounted to said frame to project outward from said frame and adapted for insertion into or into proximity of the root canal, and
   a second member for covering said heating probe, said second member being a retractable cover connected to said first member and having a first position in which said cover covers said heating probe and a second retracted position in which said heating probe is exposed.

2. The apparatus of claim 1, wherein said first member is a cylindrical tube.

3. The apparatus of claim 1, wherein said heating probe has a first portion extending parallel to axis of said first member and a second portion adjacent said first portion extending at an angle to said first portion.

4. The apparatus of claim 1, further comprising heating means arranged in connection with said frame for heating said heating probe.

5. The apparatus of claim 4, further comprising
   power means arranged in connection with said frame for providing power to said heating means.

6. The apparatus of claim 4, further comprising
   control means for controlling said heating means such that heating of said heating probe by said heating means is regulated.

7. The apparatus of claim 6, further comprising
   power means arranged in connection with said frame for providing power to said heating means,
   said control means comprising a switch electrically coupled to and interposed between said heating means and said power means.

8. The apparatus of claim 7, wherein said power means comprise a battery housed in said frame.

9. The apparatus of claim 1, further comprising heating means arranged in connection with said frame for heating said probe, a sensor for measuring the temperature of said probe, and a control unit coupled to said sensor and said heating means for controlling heating of said probe via said heating means depending on the temperature of said probe as measured by said sensor.

10. The apparatus of claim 1, wherein said cover defines an interior space having a size larger than a portion of said heating probe enclosed by said cover such that said cover does not contact said heating probe.

11. The apparatus of claim 1, further comprising displacement means for enabling said cover to move between the first position and the second position.

12. The apparatus of claim 11, wherein said displacement means comprise cooperating threads arranged on an outer periphery of said first member and on an inner surface of said cover.

13. The apparatus of claim 1, further comprising locking means for locking said cover in the second position.

14. The apparatus of claim 13, wherein said locking means comprise a flexible, metal bracket arranged on an outer peripheral surface of said first member, one end of said bracket being attached to the outer surface of said first member and an opposite end of said bracket being free and displaceable by flexure toward and away from the outer surface such that at least a portion of said cover insertable between the free end of said bracket and the outer surface of said first member.

15. The apparatus of claim 1, further comprising means for maintaining said cover in the first position.

16. The apparatus of claim 15, wherein said means comprise a spring arranged in said frame to urge said cover into the first position.

17. An apparatus for use in obturating a root canal, comprising a first member comprising
  a frame, and
  a heatable probe mounted to said frame to project outward from said frame and adapted for insertion into or into proximity of the root canal, and a second member for covering said heating probe, said second member being a cover slidably connected to said first member such that said cover is slidable between a position in which said cover covers said heating probe and a position in which said heating probe is exposed.

18. The apparatus of claim 17, wherein said cover comprises axially extending channels and a respective slot at each end of each of said channels, said slots extending circumferentially around at least a portion of an inner surface of said cover, said first member including projections at an upper end, each of said projections being slidable within a respective one of said channels and slots associated with said channel.

19. The apparatus of claim 17, wherein said heating probe has a first portion extending parallel to an axis of said first member and a second portion adjacent said first portion extending at an angle to said first portion.

20. The apparatus of claim 17, further comprising heating means arranged in connection with said frame for heating said heating probe.

21. The apparatus of claim 20, further comprising power means arranged in connection with said frame for providing power to said heating means.

22. The apparatus of claim 20, further comprising control means for controlling said heating means such that heating of said heating probe by said heating means is regulated.

23. The apparatus of claim 22, further comprising power means arranged in connection with said frame for providing power to said heating means, said control means comprising a switch electrically coupled to and interposed between said heating means and said power means.

24. An apparatus for use in obturating a root canal, comprising housing means defining an interior compartment, a displaceable unit comprising a heatable probe adapted for insertion into or into proximity of the root canal, and heating means for heating said probe, and displacement means for moving said unit from a first position in which said probe is inside said compartment to a second position in which said probe is exterior of said compartment.

25. The apparatus of claim 24, wherein said unit further comprises a frame on which said heating means and said probe are mounted and a battery coupled to said heating means for supplying power to said heating means.

26. The apparatus of claim 24, wherein said displacement means comprise an appendage attached to said unit and extending outside of said compartment.

27. The apparatus of claim 24, further comprising cooperating securing means arranged on said housing means and said unit for securing said unit in the first position in which said probe is inside said compartment and the second position in which said probe is exterior of said compartment.

28. The apparatus of claim 24, further comprising a pushbutton connected to said unit, said housing means including a slot having a pair of circular regions adapted to receive a spherical part of said pushbutton.

29. The apparatus of claim 28, wherein said pushbutton further comprises a rigid component connected to said unit and a spring interposed between said rigid component and said pushbutton.

* * * * *